United States Patent [19]
Kummer et al.

[11] Patent Number: 5,785,709
[45] Date of Patent: Jul. 28, 1998

[54] APPARATUS AND METHOD FOR PERFORMING A SURGICAL PROCEDURE ON BONE LESIONS

[75] Inventors: Frederick Kummer; Steven Shankman. both of New York. N.Y.

[73] Assignee: Hospital for Joint Diseases Orthopaedic Institute. New York. N.Y.

[21] Appl. No.: 526,305

[22] Filed: Sep. 11, 1995

Related U.S. Application Data

[63] Continuation-in-part of Ser. No. 58,171, May 10, 1993, abandoned.

[51] Int. Cl.$^6$ ............................................ A61B 17/56
[52] U.S. Cl. ........................... 606/56; 606/59; 606/96
[58] Field of Search ........................... 606/96, 97, 98, 606/102, 104, 80, 82, 79, 54, 55, 56, 57, 58, 59

[56] References Cited

U.S. PATENT DOCUMENTS

| | | |
|---|---|---|
| 2,607,339 | 8/1952 | Price . |
| 2,666,430 | 1/1954 | Gispert .................................. 606/96 |
| 2,697,433 | 12/1954 | Zehnder ................................ 606/96 |
| 3,814,089 | 6/1974 | Deyerle . |
| 4,037,592 | 7/1977 | Kronner . |
| 4,142,517 | 3/1979 | Stavropoulos et al. . |
| 4,612,922 | 9/1986 | Barber . |
| 4,625,718 | 12/1986 | Olerud et al. . |
| 4,628,922 | 12/1986 | Dewar .................................. 606/56 |
| 4,708,139 | 11/1987 | Dunbar, IV . |
| 4,738,253 | 4/1988 | Buechel et al. . |
| 4,768,524 | 9/1988 | Hardy ................................... 606/54 |
| 4,860,735 | 8/1989 | Davey et al. . |
| 4,920,958 | 5/1990 | Walt et al. ............................ 606/96 |
| 4,920,959 | 5/1990 | Witzel et al. . |
| 5,041,119 | 8/1991 | Frigg et al. . |
| 5,078,719 | 1/1992 | Schreiber . |
| 5,112,337 | 5/1992 | Paulos ................................... 606/96 |
| 5,242,444 | 9/1993 | MacMillan ............................ 606/61 |

FOREIGN PATENT DOCUMENTS

| | | | |
|---|---|---|---|
| 839510 | 6/1981 | U.S.S.R. | .............. 606/96 |
| 1161102 | 6/1985 | U.S.S.R. | .............. 606/96 |
| 1572575 | 6/1990 | U.S.S.R. | .............. 606/54 |
| 1715339 | 2/1992 | U.S.S.R. | .............. 606/54 |
| 9202184 | 2/1992 | WIPO | .............. 606/54 |

*Primary Examiner*—Guy V. Tucker
*Attorney, Agent, or Firm*—Stephen E. Feldman

[57] ABSTRACT

A guide assembly for surgical instruments used for performing surgical procedure on a bone having a longitudinal axis. At least one stand-off member secured to and extending from the bone is coupled to a support member holding the support member laterally from and in parallel relationship with the longitudinal axis of the bone. The support member provides a base for a locating assembly which comprises an arm a positioning member and a guide member. The arm is coupled to the support member and is movable linearly between the extremes thereof, along a path related to the longitudinal axis of the bone. The positioning member which includes a plurality of positioning apertures along its length, is defined by a constant radius equal to the distance the support member is laterally offset from the longitudinal axis of the bone. A guide member, defined by a mounting rod and a tubular guide member, is coupled to the positioning member at one of the positioning apertures with the line-or-sight of the tubular guide member aimed at a predetermined spot on the surface of the bone. The line-of-sight, which is latent, is made visible by inserting a rod in the tubular guide member in coincidence with the line-of-sight. When the line-of-sight is aimed or sighted on a predetermined spot on the surface of the bone, the rod may be removed from the tubular guide member and be replaced with a surgical instrument which is thus aligned by the tubular guide member.

13 Claims, 2 Drawing Sheets

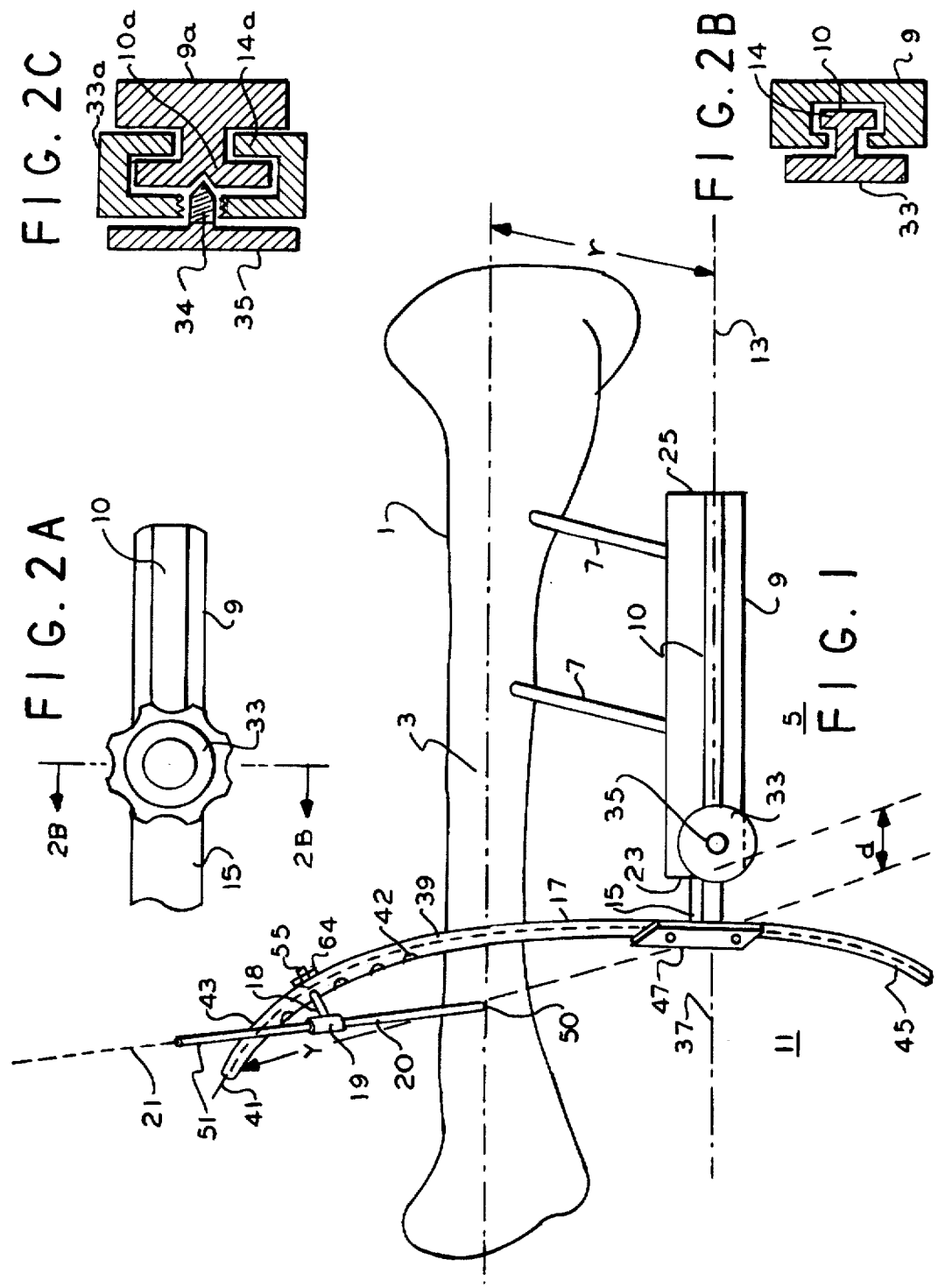

APPARATUS AND METHOD FOR PERFORMING A SURGICAL PROCEDURE ON BONE LESIONS

This application is a Continuation-in-Part of patent application Ser. No. 08/058,171, filed May 10, 1993 now abandoned.

BACKGROUND OF THE INVENTION

1. Field of the Invention

This invention relates to an apparatus and method for locating surgical instrumentation for performing surgical procedure on bone of the body. More particularly, the invention relates to apparatus for guiding surgical instrumentation to bone lesions so that a surgical procedure may be performed.

2. Prior Art

There are several guides, in the prior art, which are used in surgical procedure and particularly some which involve drilling holes on bone material.

A drill alignment apparatus adapted for osteoplastic surgery is taught in U.S. Pat. No. 4,860,735, issued to Davey, et al. This patent teaches a drill alignment apparatus for drilling into bone matter where the drill is held in a clamp which permits linear movement of the drill so that the drill bit in the drill is driven longitudinally into the bone substantially in parallel with the longitudinal axis of the bone. This apparatus is limited to drilling holes in the bone which holes are in parallel with the longitudinal axis of the bone.

U.S. Pat. No. 4,708,139, issued to Dunbar, IV teaches an adjustable slide clamp which clamps into both sides of the bone end and where one of the fingers or clamp elements of the slide clamp is tubular, to receive and guide a drill bit. The adjustable slide clamp fingers or clamp elements are in alignment so that the path of the drill bit is directly into the center of the opposing clamp finger. This limits the depth of the hole to be drilled whereby a through hole can not be drilled in the bone using this apparatus.

U.S. Pat. No. 4,037,592, issued to Kronner teaches a guide for inserting hip nails into the upper end of a femur, the hip nail for securing two pieces of the bone together. A guide tool is lowered on a pin previously inserted into the bone. The body of the guide is spring loaded with an indexed first guide mounted over the spring and an indexed second guide mounted on the first guide. The indexed first guide defines planes for taking X-ray photographs for inserting retaining pins for fixing the separated parts of the bone.

SUMMARY OF THE INVENTION

The present invention provides a guide or alignment assembly for surgical instruments used for performing a surgical procedure on a bone having a longitudinal axis. From its broadest aspects, the invention provides a support member that is offset, laterally a predetermined distance from the bone and is secured in such offset position by stand-off means, for example, bone screws and/or bone nails or other stand-off means, preferably attached to the bone and the support member. A locating assembly comprising an arm member, a positioning member and a guide member is adjustably connected to the support member, the arm member capable of moving linearly along the support member, in a line which is generally parallel to the longitudinal axis of the bone to which the support member is connected. A positioning member is secured to the arm member, the positioning member being in the form of an arcuate element which has a constant radius along its length. The radius of the arcuate element is preferably substantially equal to the distance the support member is offset from the longitudinal axis of the bone.

A guide support including a mounting rod and a tubular guide member, is mounted on the arcuate positioning member by the mounting rod. The guide member is positionable along the length of the arcuate positioning member, which length is preferably less than 360 degrees of arc. The tubular guide member has a line-of-sight which is in coincidence with the longitudinal axis of the tubular guide member. With the guide member coupled in place on the arcuate positioning member, the tubular guide member can be aimed at the bone so that the line-of-sight intersects with a predetermined or desired spot on the surface of the bone. Since the line-of-sight is latent, the line-of-sight is effectively made visible by inserting a rod in the tubular guide member, so that the inserted rod essentially becomes a visible line-of-sight extending to the bone. Since the rod inserted in the tubular guide member is, in effect the visible counterpart of the latent line-of-sight of the tubular guide member, fidelity depends upon how true or straight the rod is. The rod may be a solid rod or a tubular rod, or the rod may be in the form of a light beam. The function of a rod means is to pin-point, absolutely and visually the fall of the line-of-sight of the tubular guide member on the surface of the bone.

Once the accuracy of the line-of-sight of the tubular guide member, relative to a predetermined spot on the bone is determined, the tubular guide member may be used as a guide for surgical instruments used to perform procedures on the bone, with precision.

If the rod, which represents the line-of-sight, is tubular in construction, and the diameters permit, a surgical instrument may be passed through the rod member when the tubular guide is sighted on the desired position or location. If the rod is of solid construction, or the diameters of the elements do not permit passage, the rod may be removed from the tubular guide member and a surgical instrument may be inserted into the tubular guide member, the latter serving to guide the surgical instrument to the predetermined or desired spot on the bone.

From a less broad aspect, the invention provides a guide or aligning assemble for instruments used in performing surgical procedure on an elongated bone. The guide assembly comprising a support means and a locating assembly. The support means, which is temporally secured to and offset laterally from the bone, is positioned so that the longitudinal axis of the support means is generally parallel to and uniformly offset from the longitudinal axis of the bone to which the support means is secured by a stand-off means. The support means is temporally fixed a predetermined distance from the longitudinal axis of the bone as defined by the screws, nails and/or other stand off means coupled to both the support means and the bone.

The locating assembly comprises an arm member, a positioning member and a guide member. The arm member is mounted to the support means which provides for the arm member to slidingly move along the length of the support means, linearly and thereby move along a line which is substantially in parallel with the longitudinal axis of the bone. The positioning member is connected to the arm member and is in the form of an arcuate element defined by a constant radius, the radius being substantially equal to the distance between the longitudinal axis of the bone and the longitudinal axis of the support means. The positioning member has a plurality of positioning apertures defined by entrance and exit ports. The positioning apertures provide a means for coupling a guide support to the positioning member, selectively, along its length. The guide support includes a support rod and a tubular guide, the tubular guide being adapted to receive and retain a guide rod which, when retained in the tubular guide, extends to the bone. The tubular guide has a line-of-sight, which is latent and is made visible by inserting a rod in the tubular member so that the longitudinal axis of the rod is in coincidence with the line-of-sight of the tubular guide. The tubular guide may be adjusted so that the line-of-sight of the tubular guide is aimed at a desired spot on the surface of the bone.

The positioning apertures are adapted to receive an end portion of the guide support so that the guide support may be secured to the positioning member. The tubular guide of the guide support is aimed at or sights some spot on the surface of the bone. The tubular guide itself may be used for guiding surgical instruments to the particular, desired spot or the guide rod may be removed from the guide support and a surgical instrument can be substituted and placed in the guide support.

Precision and accuracy of the invention is preferred and since the positioning apertures are spaced, there will be radially disposed blind areas between adjacent sighted spots on the surface of the bone when all of the connected parts of the assembly are connected at normal (90 degrees) to each other. It may be necessary to fine tune the aiming of the tubular guide.

To fine tune or more precisely aim the tubular guide when required or desired, the guide support holding the tubular guide may be controllably and precisely canted or cocked in the positioning aperture of the positioning member. To accomplish this, the positioning apertures in the positioning member have been designed with an oversize exit port, oversize relative to the diameter of the end portion of the guide support, which is inserted through the positioning aperture. With the diameter of the exit port larger than the diameter of the end portion of the guide support, so as to provide a "sloppy" fit, a centering bushing or shim may be inserted on to the shaft portion of the end portion of the guide support to make the "sloppy" fit a "snug" fit. Using a normally centered centering shim or bushing, the guide support may be secured to and held in the positioning member at normal (90 degrees) to the positioning member. By using an offset or off-center centering shim or bushing the guide support may be canted or cocked from normal (90 degrees) in the positioning aperture, thus changing slightly, the orientation of the guide support and therefor changing the aim of the tubular guide.

In an alternate construction, the entrance and exit ports of the positioning apertures may be made in the same diameter and a shortened portion of the end portion of the guide support rod may be reduced in diameter, providing the same results as with different size entrance and exit ports and a uniform diameter in the end portion.

The fine tuning of the invention is accomplished without readjusting the connecting elements of the structure of the invention.

With the apparatus defined above, the method for positioning a surgical instrument with respect to a bone, preparatory to a surgical procedure comprise the steps of:

a) inserting at least one offset pin or stand off means into the bone;

b) mounting a support means on at least one offset pin or stand off means attached to the bone;

c) scanning the bone and the support means;

d) calculating the angle and distance between the support means and the area on the bone where the surgical procedure is to be performed;

e) attaching a locating assembly to the support means, f) attaching a guide rod means to the locating assembly and adjusting the guide rod to look at the required location on the bone; and g) removing the guide rod means from the locating assembly and replacing the guide rod with surgical instrument.

OBJECTS OF THE INVENTION

It is an object of the present invention to provide an improved guide assembly for performing a surgical procedure on a bone having a longitudinal axis.

Another object is to provide a surgical instrument guide assembly for use in removing lesions on a bone.

A further object of the invention is to provide an improved surgical procedure for removing lesions on a bone.

These and other objects will become apparent when reading the following detailed description of the invention with reference to the accompanying drawings.

BRIEF DESCRIPTION OF THE DRAWINGS

FIG. 1 is a simplified representation, in perspective view, of a femur and the present invention mounted thereon;

FIG. 2A is a plan view of a portion of the arm member connected to the support member shown in FIG. 1;

FIG. 2B is a cross-sectional view of the support member and the arm member along line 2B—2B of FIG. 2A;

FIG. 2C is a cross-sectional view of an alternate structure of the support member and arm member shown in FIG. 2B.

DETAILED DESCRIPTION OF THE INVENTION

Figure 3A:
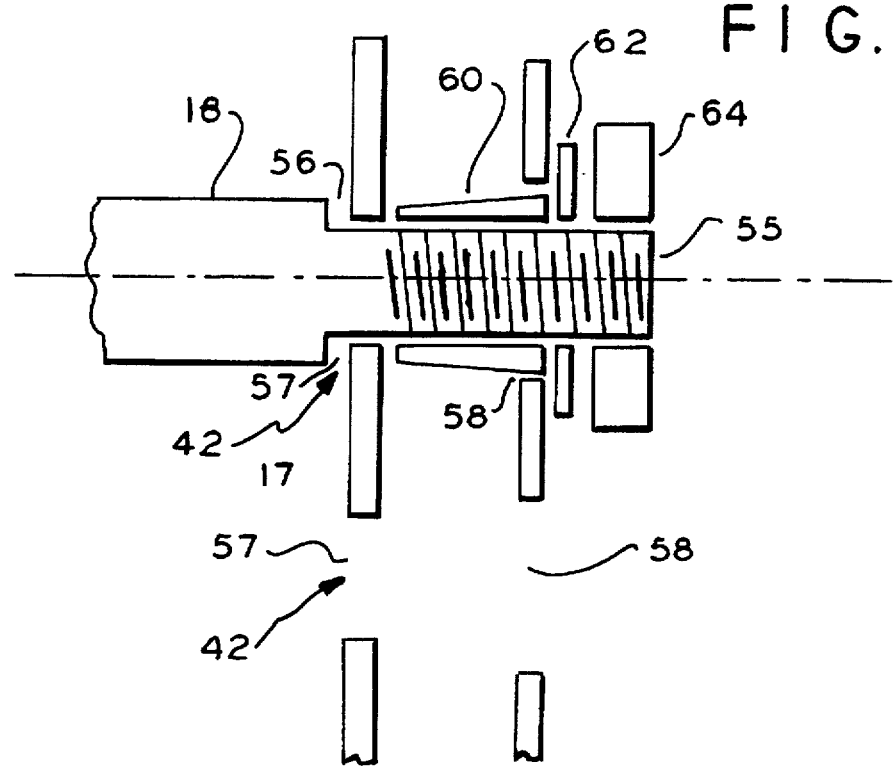
FIGS. 3A and 3B are cross-sectional views of a fine tuning apparatus for the invention.

Referring to FIG. 1, a femur bone 1 is represented having a longitudinal axis 3. A guide assembly, generally indicated by reference numeral 5, is supported by stand off members or spacers 7, such as elongated surgical pins, bone screws or bone nails, for example, inserted into the bone 1, preferably at a ninety degree angle to the longitudinal axis 3 of the bone 1. The guide assembly 5, includes a support member 9 and a locating assembly 11. The support member 9 is represented as a rectangular, planar member with a track or groove 10 essentially paralleling a longitudinal axis 13 of the rectangular planar member 9. The support member 9 could be in another geometric configuration, if desired, which will perform the same function as defined herein. The support member 9 is connected, preferably rigidly, to the stand off members 7 so that the longitudinal axis 13 of the support member, which is substantially parallel to the track 10, is essentially parallel to the longitudinal axis 3 of the bone 1, with a space or distance r between axis 3 and axis 13. Preferably, the longitudinal axis of the track 10 is in coincidence with the longitudinal axis of the support member 9.

The support member 9 is preferably in the form of a rectangular, planar member with ends 23 and 25. A track or groove 10 extends between the ends 23 and 25, essentially following the longitudinal axis 13. The track 10 may be an opening, as represented in FIG. 2B, along the face of the support member or may be in the form of a rail, as represented in FIG. 2C, extending between the ends of the support member. A runner or tongue 14 (FIG. B) or slider a (FIG. 2C) may be moved or slid along the track 10 or 10a, linearly, so as to position the locating assembly at any point between the linear extremes of the invention, as desired. The locating assembly 11 includes an arm member 15 mounted on the support member 9, a positioning member 17 and a guide 19.

The arm member 15 includes a handle 33 and a runner 14 (or slider a). The runner 14 is mounted in or on the track 10, such as represented in FIGS. B and 2C. The handle preferably includes a locking mechanism 35, one of which is represented in FIG. 2C as a threaded set pin 34 which may be screwed into the track 10a on support member 9a for locking the arm in a linear position along the track of the support member.

The positioning member 17 is connected to the arm 15. The positioning member 17 has connected thereto a guide arm 18 and a guide tube 19 which has a longitudinal axis 21. The positioning member 17 is preferably structured in the form of an elongated arcuate tubular member 39 having an arcuate longitudinal axis 41. The tubular portion of the positioning member has a plurality of spaced apertures 42 (only several of which are indicated) positioned along it length. The spaced apertures extend through the tubular member, being defined by ports 57 and 58, on opposite sides of the tube 17, each pair of ports having an axis passing therethrough which is preferably essentially in parallel with the longitudinal axis 3, of the bone 1.

The arcuate member 39 has upper and lower ends 43 and 45 which define the arcuate length of member 39. The curvature of the arcuate member follows closely, the radius r along its length. Thus, the longitudinal axis 41 of the arcuate member and the longitudinal axis 37 of the support member 9 intersect.

The positioning member 17 includes a mounting means 47, represented as guide block 47, although other clamp means may be used, if desired. The mounting means provides a means to clamp the arcuate tubular member 17 to the arm 15, which is connected or coupled to the rectangular, planar support 9 via the track/slider combination.

The guide member 19 is mounted in the positioning member 17 by passing an end portion 55 of a stud or rod 18 through any one of the positioning apertures 42. The rod 18 may include an end portion 55 and a shoulder 56 seen in FIGS. 3A and 3B, with at least part of the end portion threaded. The end portion, extending behind the shoulder, is inserted through the entrance port 57 and out the exit port 58 of the positioning aperture 42 so that the threaded end portion extends out the exit port 58 when the shoulder butts the entrance port 57, so that a threaded nut 64 may be screwed on to the threaded section of the rod, to secure the guide member 19 on to the arcuate tubular member 17. Although a tubular structure for the arcuate member is preferred, an arcuate shaped rod of solid construction may be used if desired. The guide member 19 is adapted to receive and retain a tubular rod member or guide rod 20 and aim the rod member at a desired spot on the surface of the bone 1. The rod member 20 extends through the guide member 19 so that the lower end 50 of the rod 20 may make contact with the bone or so that the lower open end 50 of the tubular guide is closely oriented to the surface of the bone 1.

Preferably, the tubular rod member 20 is held at normal (90 degrees) with the longitudinal axis 3 of the bone 1. FIG. 3A represents the rod 18 with an end portion 55 and shoulder 56. The end portion 55 is threaded and is inserted, up to the shoulder, in a positioning aperture 42. The entrance port 57 fits well, but not tight, while the exit port 58 is oversize for the diameter of the end portion 55 of the rod 18. When it is desired to hold the rod 18 at normal (90 degrees) in the positioning aperture 42, a centered, centering shim or bushing 60 is fitted over the end portion 55 to take up the "sloppy" fit. A flat washer 62 may also be used. A nut 64 may then be screw tightened, holding the rod 18 in the positioning aperture at normal, (90 degrees).

Figure 3B:
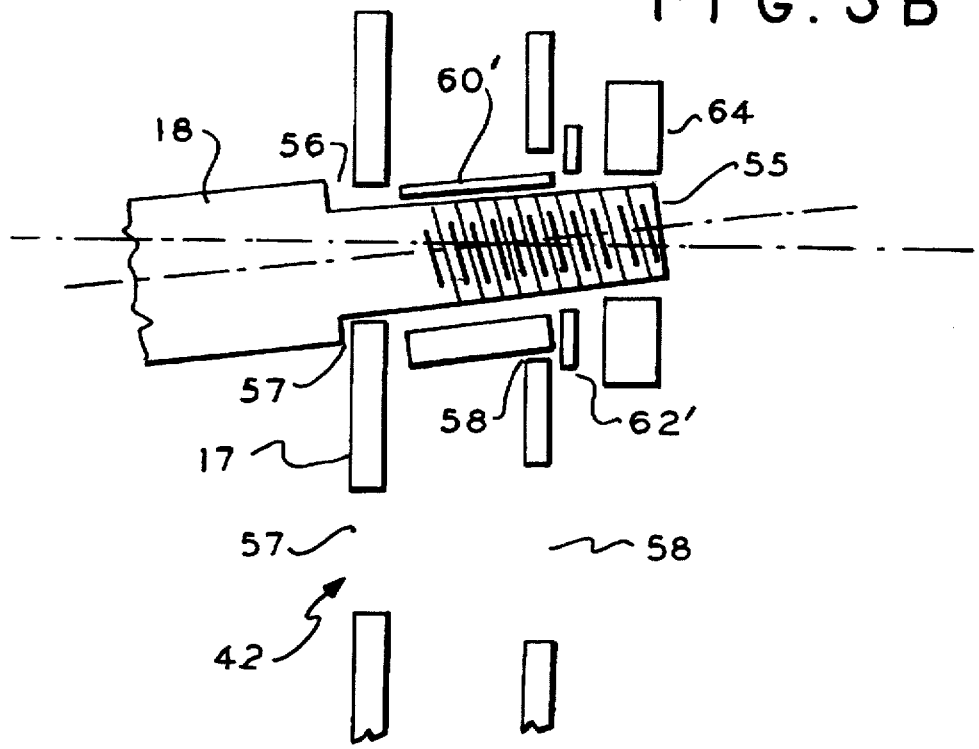

However, preferably, the platform or support member 9 is mounted parallel to the longitudinal axis of the bone and all the couplings and connections are at 90 degrees. This relates the elements of the invention to the longitudinal axis of the bone. Since the arm 15 may be positioned at any linear position along the support member 9 the linear coverage of the invention along the bone is unlimited, within the limits of the support member. However, the positioning apertures along the positioning member 17 are spaced, and blind spots in the aiming of the rod 20 exist. These blind spots are radially oriented. When the aiming of the rod 20 need be very precise and/or the aim is slightly off, or the spot on the surface of the bone at which it is desired to aim the rod 20 is a blind spot, the aim of the rod 20 may be adjusted by tilting or cocking the rod 18 in the positioning aperture. This may be controllably accomplished by using an off-centered, centering shim or bushing 60' around the end portion 55 of the rod 18, in the oversize exit port 58 on the positioning apertures 42, (FIG. 3B). This will force and hold the rod 18 off center or cocked in the positioning aperture 42 so that the rod 18 stands off normal (off 90 degrees) on the positioning member 17 so that the aim of the rod guide 20 is reoriented, radially from is normal position. By selecting an off-centered, centering bushing according to the amount of radial offset, the aim of the rod 20 may be changed linearly. By adjusting the off-centered, centering shim or bushing rotationally on the shank of the end portion 55 of the rod 18, the aim of the rod 20 may changed rotationally.

A wedge shaped washer 62' may also be used between the nut 64 and the wall of the positioning member 17. The aim of the rod 20 may be changed, within the limits of the size of the exit port.

Preferably, the size of the exit port 58 of the positioning apertures 42 relative to the entrance port 57 and to the diameter of the end portion 55 of the rod 18 is such so as to permit the adjustment to the aiming of the guide rod 20 to cover the blind spot defined by the spacing between the positioning apertures so that full radial coverage of the bone is attained. Thus, the precision of the aiming capability of the invention is absolute.

A preferred method of positioning a surgical instrument, such as a drill rod member (not shown), with respect to the bone 1, preparatory to a surgical procedure, such as removing localized bone lesions, comprises the following steps:

a) a pair of spaced surgical pins 7 are inserted into the bone 1 so that they are essentially perpendicular to the longitudinal axis of the bone;

b) the support member 9 is fixedly mounted on the two pins 7;

c) the region of the bone 1 where the bone lesions are present and the support member 9 are scanned;

d) the angle "a" and the distance "d" between the support member 9 and the bone lesions are calculated based on information provided by the scan;

e) the locating assembly 11 is attached to the support member 9 and the arm 15 is moved linearly between the ends 23 and 25 of the support member 9 and the guide member 19 is positioned on the arcuate positioning member 17 at an angle "a";

f) the guide rod member 20 is disposed through the guide member 19 so that the lower end 50 of the rod guide 20 is positioned against or closely adjacent the bone 1, where the lesions are present;

g) step "c" is repeated to determine whether the guide rod 20 is properly positioned against the bone where the lesions are present; and h) remove the guide rod 20 from the guide member 19 and substitute a surgical instrument therefore.

A variety of sizes of drill bits are available for use in removing lesions that can be present on a bone. If the rod guide 20 is tubular, the dill bit may be inserted in the rod guide if the diameter of the drill bit is sufficiently small to fit into the inside the rod guide. In such event the step h) could be:

h') insert a surgical instrument (drill bit) into the upper end 51 of the rod guide 20, moving the instrument down through the rod guide to the bone 1.

Thus there has been described an apparatus and method for positioning surgical instrument, with great precision, on or against a bone for the purpose of performing a surgical procedure on the bone. A preferred embodiment has been shown and described along with alternate structure. Other changes and modifications may be made, as will become apparent to those skilled in the art, without departing from the spirit of the invention defined in the claims.

What is claimed is:

1. An apparatus for performing a surgical procedure on bone lesions comprising:

(a) a generally planar support means having an upper face and a lower face, said upper face having a central groove formed therein intermediate the ends of said support means;

(b) spaced apart, elongated spacer means secured to the lower face of said support means, said spacer means being capable of being secured to a bone upon which a surgical procedure is to be performed such that the longitudinal axis of said support means is maintained substantially parallel to the longitudinal axis of a bone to which said spacer means are secured;

(c) an elongated, tubular, arcuate positioning member having a plurality of spaced apertures formed therein along its arcuate length intermediate its ends, said apertures extending through said arcuate positioning member, each of said apertures having an entrance port and an exit port;

(d) means to mount said arcuate positioning member in sliding engagement within the groove of said support means enabling said arcuate positioning member to be moved linearly along said groove;

(e) a lock means on said support means to secure said arcuate positioning member at pre-determined positions along the groove of said support means;

(f) a generally T-shaped support member the short leg of which is tubular and the long leg of which is in the form of a rod having an end portion and a shoulder portion, said long leg being capable of being inserted into and through an aperture in said arcuate positioning member; and, (g) an elongated, tubular guide member secured within the short leg of said T-shaped support member such that the longitudinal axis of said guide member is disposed perpendicular to a bone upon which a surgical procedure is to be performed with the lower end of said guide member closely oriented to the surface of said bone.

2. The apparatus of claim 1 wherein the end of the long leg of said T-shaped support member is threaded to receive a threaded nut thereon to secure said support member to said arcuate positioning member.

3. The apparatus of claim 1 wherein said exit port is oversize with respect to the end portion of said T-shaped support member and includes a centering shim for centering said end portion in said exit port.

4. The apparatus of claim 3 wherein said centering shim has an aperture formed therethrough enabling said centering shim to be fitted on said end portion, said aperture being offset from the center axis of said centering shim enabling said T-shaped support member to be canted in said aperture.

5. The apparatus of claim 4 wherein said centering shim is rotatable enabling the attitude of said T-shaped support member to be changed.

6. The apparatus of claim 1 wherein the arc of said arcuate positioning member is less than 180 degrees.

7. The apparatus of claim 1 wherein said spacer means are bone screws.

8. The apparatus of claim 1 wherein said spacer means are bone pins.

9. An apparatus for performing a surgical procedure on bone lesions comprising:

(a) a generally planar support means having an upper face and a lower face, said upper face having a central groove formed therein intermediate the ends of said support means;

(b) spaced apart, elongated spacer means secured to the lower face of said support means, said spacer means being capable of being secured to a bone upon which a surgical procedure is to be performed such that the longitudinal axis of said support means is maintained substantially parallel to the longitudinal axis of a bone to which said spacer means are secured;

(c) an elongated, tubular, arcuate positioning member having an arc of less than 180 degrees and a plurality of spaced apertures formed therein along its arcuate length intermediate its ends, said apertures extending through said arcuate positioning member, each of said apertures having an entrance port and an exit port, said exit ports being oversized and including a centering shim;

(d) means to mount said arcuate positioning member in sliding engagement within the groove of said support means enabling said arcuate positioning member to be moved linearly along said groove;

(e) lock means on said support means to secure said arcuate positioning member at pre-determined positions along the groove of said support means;

(f) a generally T-shaped support member the short leg of which is tubular and the long leg of which is in the form of a rod having an end portion and a shoulder portion, said long leg being capable of being inserted into and through an aperture in said arcuate positioning member and being threaded to receive a threaded nut thereon in securing said support member to said arcuate positioning member and enabling said centering shim to center said end portion in said exit port; and, (g) an elongated, tubular guide member secured within the short leg of said T-shaped support member such that the longitudinal axis of said guide member is disposed perpendicular to a bone upon which a surgical procedure is to be performed with the lower end of said guide member closely oriented to the surface of said bone.

10. The apparatus of claim 9 wherein said centering shim has an aperture formed therethrough enabling said centering shim to be fitted on said end portion, said aperture being offset from the center axis of said centering shim enabling said T-shaped support member to be canted in said aperture.

11. The apparatus of claim 10 wherein said centering shim is rotatable enabling the attitude of said T-shaped support member to be changed.

12. The apparatus of claim 9 wherein said spacer means are bone screws.

13. The apparatus of claim 9 wherein said spacer means are bone pins.

* * * * *